United States Patent [19]

Mitschke et al.

[11] 4,168,277
[45] Sep. 18, 1979

[54] PRODUCTION OF TETRAETHYL AMMONIUM PERFLUOROALKYL SULPHONATE

[75] Inventors: Karl-Heinz Mitschke, Odenthal; Hans Niederprüm, Monheim; Johann-Nikolaus Meussdoerffer, Leverkusen, all of Fed. Rep. of Germany

[73] Assignee: Bayer Aktiengesellschaft, Leverkusen, Fed. Rep. of Germany

[21] Appl. No.: 858,499

[22] Filed: Dec. 7, 1977

[30] Foreign Application Priority Data

Dec. 23, 1976 [DE] Fed. Rep. of Germany ....... 2658560

[51] Int. Cl.$^2$ ............................................. C07C 87/30
[52] U.S. Cl. ................................................. 260/501.15
[58] Field of Search ..................................... 260/501.15

[56] References Cited

U.S. PATENT DOCUMENTS

| 3,346,612 | 10/1967 | Hansen ................................. 260/456 |
| 3,723,512 | 3/1973 | Niederprum et al. .......... 260/501.15 |

FOREIGN PATENT DOCUMENTS 1966931 6/1969 Fed. Rep. of Germany ...... 260/501.15

OTHER PUBLICATIONS

Beyl et al., Liebigs Ann. Chem., 731, pp. 58–66, 1970.
Gramstad et al., J. Chem. Soc., p. 2640, 1957.

*Primary Examiner*—James O. Thomas, Jr.
*Assistant Examiner*—G. T. Breitenstein
*Attorney, Agent, or Firm*—Sprung, Felfe, Horn, Lynch & Kramer

[57] ABSTRACT

Production of tetraethyl ammonium perfluoroalkyl sulphonates $(C_2H_5)_4N^{\oplus}R_FSO_3^{\ominus}$, wherein $R_F$ represents a perfluorinated alkyl radical with about 4 to 10 carbon atoms, by reacting crude perfluoroalkyl sulphonic acid fluoride, i.e. perfluoroalkyl sulphonic acid fluoride which has not been especially purified, with triethylamine and an ethoxy silane, preferably dimethyl diethoxy silane, methyl triethoxy silane or tetraethoxy silane in an inert solvent at temperatures of about 10° to 60° C., preferably about 20° to 40° C. The process according to the invention is particularly suitable for the production of tetraethyl ammonium perfluorooctane sulphonate.

2 Claims, No Drawings

PRODUCTION OF TETRAETHYL AMMONIUM PERFLUOROALKYL SULPHONATE

The production of perfluoroalkyl-substituted quaternary ammonium salts by reacting perfluoroalkyl sulphonyl fluorides with alkoxy silanes and tertiary amines is taught per se in German Offenlegungsschrift Nos. 1,929,665 and 1,966,931, and Liebigs Ann. Chem. 731, 58–66 (1970). In this process, a mixture of perfluoroalkyl sulphofluoride, methyl triethoxy silane and triethylamine is reacted, for example in chlorobenzene, at reaction temperatures of around 100° C. in accordance with the following equation:

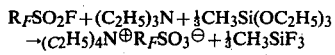
$$R_FSO_2F + (C_2H_5)_3N + \tfrac{1}{3}CH_3Si(OC_2H_5)_3 \rightarrow (C_2H_5)_4N^{\oplus}R_FSO_3^{\ominus} + \tfrac{1}{3}CH_3SiF_3$$

The methyl trifluorosilane formed escapes in gaseous form. Now, it is known that particularly the higher members of the perfluoroalkane sulphonyl fluoride series with chain lengths in excess of two carbon atoms, owing to their production by electrochemical fluorination in anhydrous HF, contain impurities which are highly sensitive to strong bases and therefore show a tendency towards tar formation (Liebigs Ann. Chem., No. 1 (1972), page 20). According to U.S. Pat. No. 3,346,612 (Example A), therefore, it is proposed to purify the higher members of the perfluoroalkyl sulphonyl fluorides, more especially the perfluorooctane sulphofluoride which is a commercially important intermediate product for the production of fluorine surfactants, by a preliminary treatment with boiling triethylamine and pyridine, followed by washing with dilute hydrochloric acid or heated concentrated sulphuric acid. According to U.S. Pat. No. 3,346,612, it is only this purified perfluorooctane sulphofluoride which can be used for the production of perfluorooctane sulphonic acid aryl esters by reaction with phenols and, for example, triethylamine.

In the absence of this treatment, i.e. in cases where the compound used is, for example, a perfluorooctane sulphofluoride which has only been separated off by distillation from the crude electrolysis product formed by fluorination of octane sulphochloride, the products formed may still be contaminated and, for this reason, are unsuitable, for example, for photographic or galvanic applications where only very pure surfactants can be used.

The nature of the troublesome impurities in perfluorooctane sulphonyl fluoride is partly known. According to Haszeldine et al., J. Chem. Soc. 1957, 2640, the electrofluorination of octane sulphochloride is accompanied by the formation not only of perfluoroalkanes and relatively short-chain fluorinated sulphofluorides, but also, through oxidation and radical reactions, of fluorinated carbonyl fluorides, which are converted into carboxylic acids during the usual washing with water to remove HF, and of relatively long-chain fluorinated disulphofluorides and polymeric products. Under strongly basic reaction conditions, these compounds can enter into elimination and rearrangement reactions which give rise to heavy discoloration.

Although perfluorooctane sulphofluoride can be purified by the pretreatment with amine described in U.S. Pat. No. 3,346,612, this method is nevertheless attended by significant disadvantages. Firstly, the treatment with pyridine/triethylamine results in the formation of a deep black reaction mixture which can only be subjected with difficulty to phase separation, resulting in considerable losses of yield. The repeated aftertreatment with acids can give rise to further losses during separation of the fluorocarbon phase of high specific gravity, which is a considerable economic disadvantage in view of the high price of long-chain perfluorocarbon compounds. In addition, the amines added, especially triethylamine, chemically attack the perfluorooctane sulphofluoride itself in view of the long reaction time. Although fluorinated sulphonyl halides are considerably more chemically and thermally stable than non-fluorinated compounds, reactions can nevertheless occur, for example with elimination of $SO_2$, under intensified conditions.

Moreover, the described pretreatment with amines is accompanied by the formation of dark colored decomposition products formed from the fluorine compounds present and these are difficult to eliminate without polluting the environment.

The present invention provides a process for the production of tetraethyl ammonium perfluoroalkyl sulphonates by reacting perfluoroalkyl sulphonyl fluoride with triethylamine and alkoxy silane, wherein crude non-purified perfluoroalkyl sulphonyl fluoride is reacted with a stoichiometric excess of ethoxy silanes in an inert solvent at temperatures of from about 10° to 60° C.

It has surprisingly been found that, in the production of highly pure, substantially colorless tetraethyl ammonium perfluoroalkyl sulphonate, especially tetraethyl ammonium perfluorooctane sulphonate, it is possible to start with crude, possibly only distilled perfluoroalkyl sulphonyl fluoride, such as for example perfluorooctane sulphonyl fluoride or perfluorobutane sulphonyl fluoride, providing there is used a temperature of about 10° to 60° C. and a large excess of the ethoxy silicon compound which is generally quite inexpensive. The mixture is preferably reacted at temperatures of about 20° C. to 40° C. The excess, based on the reaction equation shown above, should be so great that one ethoxy group, or even two groups where tetraethoxy silane or methyltriethoxy silane is used, in the polyfunctional silicic acid ester compound is replaced by fluorine, for example in accordance with the following equation:

$$C_8F_{17}SO_2F + (C_2H_5)_3N + CH_3Si(OC_2H_5)_3 \rightarrow (C_2H_5)_4N^{\oplus}C_8F_{17}SO_3^{\ominus} + CH_3SiF(OC_2H_5)_2$$

The fluorosilane formed remains in the mother liquor, while the tetraalkyl ammonium perfluoroalkyl sulphonate crystallizes out providing suitable solvents have been used. Suitable solvents are, for example, chlorobenzene, ethers, toluene, etc.

The starting material is of the formula $R_FSO_2F$ wherein $R_F$ is a perfluoroalkyl radical of up to about 10 carbon atoms. While the reaction proceeds even with perfluoromethyl sulphonyl fluoride, the invention is of greatest benefit where $R_F$ has at least about 4 and preferably about 8 carbon atoms. The co-reactant is an ethoxy silane such as tetraethoxy silane or a methyl ethoxy silane such as dimethyl diethoxy silane or methyl triethoxy silane and its stoichiometric excess will depend upon the nature and amount of impurity but generally it has at least about 10% and preferably at least about 20% more ethoxy silane molecules than are required for reaction with all the sulphonyl fluoride.

It is remarkable that even crude, non-distilled electrolysis products which have been freed from hydrogen fluoride merely by washing and then drying can be successfully reacted to form substantially pure tetraethyl ammonium perfluoroalkyl sulphonate, although in general they only contain approximately 60% of $R_FSO_2F$.

The products produced in accordance with the invention may be used for a variety of industrial applications. The octyl derivative is used, for example, as an agent for suppressing chromium mist in electro-chromium-plating, especially so-called skin chromium plating, e.g. German Offenlegungsschrift No. 2,508,708 and Metalloberflache 29 (1975), 559–567, as an internal mold-release agent in the injection molding of thermoplasts such as polycarbonates, as wetting agents in the acid polishing of glass and in photographic emulsions (German Offenlegungsschrift No. 2,506,726; ChemInform 7/1976, page 61). The corresponding $C_4$-derivative is used, for example, as a conducting salt in polarography.

The process according to the invention is illustrated by the following examples:

EXAMPLE 1

108.5 g (0.2 mole) of perfluorooctane sulphonyl fluoride which has been distilled, but not especially purified with amines (purity as determined by gas chromatography: 92.25%), 42.6 g (0.24 mole, 20% excess) of methyl triethoxy silane and 25.2 g (0.25 mole) of triethylamine were combined in the absence of moisture in 400 ml of dry chlorobenzene. The two-phase mixture was then left standing for about 8 hours with thorough stirring. A weakly exothermic reaction initially took place. The reaction temperature was limited to a maximum of 35° C. by means of a thermostatically controlled cooling bath. The readily filtrable deposit which had precipitated was then separated off and washed with approximately 300 ml of chlorobenzene. After drying in a vacuum drying cabinet at a maximum temperature of 60° C. (20 Torr), it was possible to isolate 116 g (92% of the theoretical amount) of almost white $(C_2H_5)_4N^{\oplus}C_8F_{17}SO_3^{\ominus}$. Quantitative analysis revealed only traces of inorganic fluorine.

| Nuclear resonance spectrum | |
|---|---|
| $\overset{b}{\oplus}N(\overset{a}{CH_2}-\overset{a}{CH_3})_4$ $\overset{a'}{CF_3}-\overset{f'}{CF_2}-\overset{e'}{CF_2}(\overset{d'}{CF_2})_3-\overset{c'}{CF_2}-\overset{b'}{CF_2}-SO_3^{\ominus}$ | |
| Signal: $1_H$ | $19_F$ |
| (a) 1.20 ppm | (a') + 5.8 ppm |
| (b) 3.23 ppm | (b') + 39.6 ppm |
|  | (c') + 45.7 ppm |
|  | (d') + 47.0 ppm |
| Solvent DMSO-$d_6$ | (e') + 47.8 ppm |
|  | (f') + 51.6 ppm |

The single-phase brown filtrate was subjected to fractional distillation along with the $CO_2$/acetone-cooled contents of the trap used for drying. In addition to 3.4 g of unreacted $C_8F_{17}SO_2F$, it was possible to detect the compound $CH_3SiF(OC_2H_5)_2$, b.p. approximately 70° C., in the first runnings from the recovery of chlorobenzene and, in addition, small quantities of the hydrolysis product

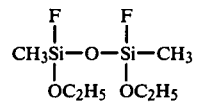

and also ethanol.

EXAMPLE 2

42.6 g (0.24 mole, 20% excess) of methyl triethoxy silane, 25.2 g (0.25 mole, 25% excess) of triethylamine and 400 ml of dry chlorobenzene were added to a vessel, followed by the dropwise addition with vigorous stirring over a period of 2 hours at room temperature of 160 g (0.2 mole) of nondistilled, crude perfluorooctane sulphonyl fluoride with a purity as determined by gas chromatography of 63±2% (the impurities being perfluoroalkanes and shorter-chain and longer chain sulphonyl fluorides). A slight increase in temperature up to about 40° C. resulted. The reaction was completed by stirring for 10 hours at room temperature. After standing overnight, the crystalline, readily filtrable deposit was separated off and washed with 50 ml of chlorobenzene. After drying to constant weight at 70° C./20 Torr, 132 g of an almost white salt were obtained, m.p. 190°–192° C. Analysis showed an organic fluorine content of only 0.013%.

EXAMPLE 3

49.9 g (0.24 mole) of tetraethoxy silane, 25.2 g (0.25 mole) of triethylamine, 160 g of crude perfluorooctane sulphonyl fluoride with the composition indicated in Example 2 and 400 ml of chlorobenzene were reacted for 8 hours with thorough stirring. 122 g of a product consisting essentially of tetraethyl ammonium perfluorooctane sulphonate were isolated. The compound $(C_2H_5O)_3SiF$ could be detected in the filtrate.

EXAMPLE 4

The reactants were reacted as in Example 3, the only difference being that the quantity of tetraethoxy silane was limited to 25 g (0.12 mole), corresponding to the formation of $(C_2H_5O)_2SiF_2$. 109 g of product which also consisted essentially of tetraethyl ammonium perfluorooctane sulphonate were isolated.

It will be appreciated that the instant specification and examples are set forth by way of illustration and not limitation, and that various modifications and changes may be made without departing from the spirit and scope of the present invention.

What is claimed is:

1. A process for the production of a tetraethyl ammonium perfluoroalkyl sulphonate comprising reacting a perfluoroalkyl sulphonyl fluoride with triethylamine and an ethoxysilane selected from the group consisting of dimethyldiethoxysilane, methyltriethoxysilane and tetraethoxysilane, the perfluoroalkyl sulphonyl fluoride being of a purity of the order of about 60% and being an electrolysis product from an anodic fluorination of an octane sulphohalide in anhydrous hydrogen fluoride, the ethoxysilane being employed in at least about a 20% stoichiometric excess, the reaction being effected in an inert solvent medium and at a temperature of about 10° C. to 60° C.

2. A process as claimed in claim 1, wherein the temperature is about 20° to 40° C. and the solvent is chlorobenzene, toluene or ether.

* * * * *